US008658812B2

(12) United States Patent
Brüning et al.

(10) Patent No.: US 8,658,812 B2
(45) Date of Patent: Feb. 25, 2014

(54) WAX DISPERSIONS

(75) Inventors: Stefan Brüning, Philadelphia, PA (US);
Marco Capito, Düsseldorf (DE);
Roland Spörer, Kleinenbroich/Glehn (DE); Achim Ansmann, Erkrath (DE);
Mark Leonard, Bexley/Kent (GB)

(73) Assignee: Cognis IP Management GmbH, Duesseldorf (DE)

( * ) Notice: Subject to any disclaimer, the term of this patent is extended or adjusted under 35 U.S.C. 154(b) by 1324 days.

(21) Appl. No.: 10/541,111

(22) PCT Filed: Dec. 19, 2003

(86) PCT No.: PCT/EP03/14596
§ 371 (c)(1),
(2), (4) Date: Jun. 30, 2005

(87) PCT Pub. No.: WO2004/062630
PCT Pub. Date: Jul. 29, 2004

(65) Prior Publication Data
US 2006/0116524 A1 Jun. 1, 2006

(30) Foreign Application Priority Data

Jan. 8, 2003 (DE) .................................. 103 00 506

(51) Int. Cl.
*C10L 1/16* (2006.01)
(52) U.S. Cl.
USPC .......................................................... 554/166
(58) Field of Classification Search
USPC ................... 554/166; 585/9; 106/271
See application file for complete search history.

(56) References Cited

U.S. PATENT DOCUMENTS

| 2,844,534 | A | * | 7/1958 | Young et al. .................. 508/433 |
| 4,919,923 | A | * | 4/1990 | Hoeffkes et al. .............. 424/70.1 |
| 4,996,004 | A | * | 2/1991 | Bucheler et al. .............. 424/401 |
| 5,306,488 | A | | 4/1994 | Vanlerberghe et al. |
| 5,474,778 | A | * | 12/1995 | Ichikawa et al. .............. 424/401 |
| 5,478,555 | A | | 12/1995 | Bara et al. |
| 5,743,949 | A | * | 4/1998 | Kainz ........................... 106/271 |
| 5,840,285 | A | * | 11/1998 | Fogel ............................. 424/64 |
| 5,840,943 | A | | 11/1998 | Ansmann et al. |
| 6,207,014 | B1 | | 3/2001 | De Haut et al. |
| 6,280,712 | B1 | | 8/2001 | Ansmann et al. |
| 6,365,168 | B1 | * | 4/2002 | Ansmann et al. ............. 424/401 |
| 6,562,876 | B1 | * | 5/2003 | Ansmann et al. ............. 516/77 |
| 6,835,700 | B1 | | 12/2004 | Nieendick et al. |
| 6,953,500 | B2 | * | 10/2005 | Lewis ............................ 106/3 |
| 2002/0055560 | A1 | | 5/2002 | Nanbu et al. |
| 2002/0072544 | A1 | * | 6/2002 | Miller et al. ................... 516/21 |
| 2003/0118534 | A1 | * | 6/2003 | Bruning et al. ................ 424/66 |
| 2003/0161801 | A1 | * | 8/2003 | Yamasaki et al. ............. 424/65 |
| 2004/0086470 | A1 | * | 5/2004 | Nieendick et al. ............ 424/63 |
| 2004/0116542 | A1 | * | 6/2004 | Baumoeller et al. .......... 516/77 |

FOREIGN PATENT DOCUMENTS

| CA | 1333570 | | 12/1994 |
| DE | 33 09 530 | C1 | 10/1984 |
| DE | 44 11 557 | A1 | 10/1995 |
| DE | 195 11 668 | A1 | 10/1996 |
| DE | 19730423 | C1 | 12/1998 |
| DE | 197 37 737 | A1 | 3/1999 |
| DE | 198 31 705 | A1 | 3/1999 |
| DE | 198 37 191 | A1 | 2/2000 |
| DE | 10058224 | A1 * | 5/2002 |
| DE | 199 43 585 | B4 | 8/2004 |
| EP | 0 394 078 | B1 | 10/1990 |
| EP | 0 766 661 | B1 | 4/1997 |
| EP | 0832643 | A2 | 4/1998 |
| JP | 02-022211 | A | 1/1990 |
| JP | 04360821 | A | 12/1992 |
| JP | 09-503767 | A | 4/1995 |
| JP | 10-101525 | A | 4/1998 |
| JP | 10298031 | A | 11/1998 |
| JP | 2000-511913 | A | 9/2000 |
| JP | 2000269221 | A | 9/2000 |
| JP | 2001-505257 | A | 4/2001 |
| JP | 2002-544325 | A | 12/2002 |
| WO | 95/10259 | A1 | 4/1995 |
| WO | WO 95/16824 | A1 | 6/1995 |
| WO | WO 95/35411 | A1 | 12/1995 |
| WO | WO 95/35412 | A1 | 12/1995 |
| WO | 96/24723 | A1 | 8/1996 |
| WO | WO 97/30216 | A1 | 8/1997 |
| WO | 97/47274 | A2 | 12/1997 |
| WO | WO 98/20840 | A2 | 5/1998 |

(Continued)

OTHER PUBLICATIONS

MSDS Sodium Lauryl Ether Sulfate (2000).*
Mathis, "Paradigm Shift in Finishes for Coverstock: Active Care Instead of Harmlessness", Nonwovens World, (Oct.-Nov. 1999), pp. 59-62 & 65.
Shaikh et al., "Organic Carbonates", Chem. Rev., vol. 96, (1996), pp. 951-976.

(Continued)

*Primary Examiner* — Melvin C Mayes
*Assistant Examiner* — Stefanie Cohen
(74) *Attorney, Agent, or Firm* — Servilla Whitney LLC

(57) ABSTRACT

The disclosed invention provides wax dispersions with an average particle size of 0.5 to 100 μm containing (a) a wax phase with a melting point above 25° C. which contains at least one oil or wax component selected from dialkyl(ene) ethers, dialkyl(ene) carbonates, dicarboxylic acids, hydroxy-fatty alcohols, and mixtures thereof and at least one emulsifier, and (b) a water phase. The wax dispersions are particularly useful as a basis for cosmetic preparations and, more particularly, for impregnating and wetting utility and sanitary wipes used for personal hygiene and body care.

25 Claims, No Drawings

(56) References Cited

FOREIGN PATENT DOCUMENTS

| WO | WO 00/10510 A1 | 3/2000 |
| WO | 0100149 A1 | 1/2001 |
| WO | WO 0158417 A1 * | 8/2001 |
| WO | 02/43672 | 6/2002 |
| WO | WO 02/056839 A2 | 7/2002 |
| WO | WO 02056839 A2 * | 7/2002 |
| WO | WO 02056841 A2 * | 7/2002 |
| WO | WO 03/037292 A1 | 5/2003 |

OTHER PUBLICATIONS

Kirk-Othmer, Encyclopedia of Chemical Technology, 3rd Ed., vol. 8, (1979), pp. 913-915.

CD RÖMPP Chemie Lexikon—Version 1.0, Stuttgart, New York: Georg Thieme Verlag (1995).

* cited by examiner

WAX DISPERSIONS

CROSS-REFERENCE TO RELATED APPLICATIONS

This application claims priority under 35 USC §365 from International Application PCT/EP2003/014596, filed on Dec. 19, 2003, which claims priority from German Application No. 103 00 506.4, filed on Jan. 8, 2003.

BACKGROUND OF THE INVENTION

1. Technical Field

This invention relates to special wax dispersions which may be used as a basis for cosmetic preparations and, more particularly, for impregnating and wetting utility and sanitary wipes used for personal hygiene and body care.

2. Background Art

The generic term "paper" encompasses about 3,000 different types and articles which can differ, sometimes considerably, in their applications and their properties. Their production involves the use of numerous additives among the most important of which are fillers (for example chalk or kaolin) and binders (for example starch). For tissues and hygiene papers, which come into relatively close contact with the human skin, there is a particular need for an agreeable soft feel which is normally given to the paper by careful selection of the fibers and, in particular, by a high percentage of fresh mechanical wood pulp or cellulose. However, in the interests of economic paper manufacture and from the ecological perspective, it is desirable to use large amounts of inferior-quality deinked wastepaper. Unfortunately, this means that the softness of the paper is significantly reduced which is troublesome in practice and can even lead to irritation of the skin, particularly with frequent use.

Accordingly, there has been no shortage of attempts in the past to treat tissue papers by impregnation, coating or other surface treatments in such a way that a more agreeable sensory impression is achieved. This requires the development of special lotions and emulsions which, on the one hand, are easy to apply to the paper and, on the other hand, do not adversely affect its structure. Softness is often improved by the use of nonionic surfactants or a combination of nonionic and anionic surfactants. Polysiloxanes and cationic polymers are also used for this purpose.

International patent application WO 95/35411 relates to tissue papers coated with softening formulations which contain 20 to 80% by weight of a water-free emollient (mineral oils, fatty acid esters, fatty alcohol ethoxylates, fatty acid ethoxylates, fatty alcohols and mixtures thereof), 5 to 95% by weight of an "immobilizing agent" for the emollient (fatty alcohols, fatty acids or fatty alcohol ethoxylates containing 12 to 22 carbon atoms in the fatty component) and 1 to 50% by weight of surfactants with an HLB value of preferably 4 to 20. The Examples of this document all contain petrolatum as emollient. International patent application WO 95/35412 discloses similar tissue papers where water-free mixtures of (a) mineral oils, (b) fatty alcohols or fatty acids and (c) fatty alcohol ethoxylates are used as softeners. International patent application WO 95/16824 describes softening formulations for tissue papers containing mineral oil, fatty alcohol ethoxylates and nonionic surfactants (sorbitan esters, glucamides). In addition, International patent application WO 97/30216 (Kaysersberg) describes liquid softening formulations for paper handkerchiefs based on long-chain saturated fatty alcohols and wax esters with, in all, at least 24 carbon atoms which have a very high water content. DE 33 09 530 describes hygienic absorbent materials which are coated with glycerides and/or partial glycerides of coconut oil fatty acids. Coatings for personal hygiene products are also described by R. E. Mathis in Nonwovens World 1999, pages 59-65.

From the performance perspective, however, the sensory properties of the treated papers and tissues are still in need of improvement. The coatings in use at present are unsatisfactory in their skin-care effect and often leave the skin feeling too greasy and, in some cases, are distinguished by an overly slow release of active ingredients. In the field of baby hygiene in particular, the effective release of active components, an improved care effect and better sensory properties are very important requirements. The long-term stability of the coated wipes in storage is also in need of improvement. The coating should not sink to the bottom of the storage container in the event of prolonged storage. From the manufacturing perspective, the application behavior of the compositions is unsatisfactory. In particular, there is a need to develop coatings which can be applied cold and, hence, are less expensive to produce and also emit fewer odors.

The problem addressed by the present invention was to provide compositions for coating tissue papers for the production of wet wipes and dry wipes which would be distinguished by improved sensory properties and, more particularly, by a caring, non-troublesome and less greasy feeling on the skin. In addition, the compositions would be able to be applied particularly easily to substrates. The coated papers/wipes would have excellent care properties and would be distinguished by the efficient release of active components and by particular mildness and dermatological compatibility. In addition, only readily biodegradable auxiliaries would be used and the preparations would readily penetrate into the tissue, would be uniformly distributed and would be readily processable.

BRIEF SUMMARY OF THE INVENTION

It has been found that wax dispersions which contain special oil or wax components and which have a particle size in the micrometer range possess excellent sensory and care properties, are very easy to apply to substrates and are therefore particularly suitable for impregnating papers and wipes for the body care field.

Accordingly, the present invention relates to wax dispersions with an average particle size of 0.5 to 100 μm containing (a) a wax phase with a melting point above 25° C. which contains at least one oil or wax component selected from dialkyl(ene) ethers, dialkyl(ene) carbonates, dicarboxylic acids or hydroxyfatty alcohols or a mixture of these substances and at least one emulsifier, (b) water phase.

DETAILED DESCRIPTION OF THE INVENTION

In a preferred embodiment, the wax dispersions according to the invention contain (a) 1 to 75% by weight of a wax phase with a melting point above 25° C. which contains at least one oil or wax component selected from dialkyl(ene) ethers, dialkyl(ene) carbonates, dicarboxylic acids or hydroxyfatty alcohols or a mixture of these substances and at least one emulsifier and 25 to 99% by weight of a water phase, based on the overall composition. Preferred wax dispersions according to the invention contain 5 to 30% by weight of the above wax phase, a content of 10 to 25% by weight of the wax phase, based on the wax dispersion, being particularly preferred.

In the manufacturing process, the wax dispersions according to the invention may be applied to such substrates as papers and tissues in fine distribution, in cold-processable form and more easily than a melt of waxes. They may be applied both in the form of concentrates with a water content of only 25% by weight and also in highly diluted form, for example in a concentration of only 1% by weight. The wax dispersions according to the invention are optimized in their sensory properties by combination with special oil and wax components selected from dialkyl(ene) ethers, dialkyl(ene) carbonates, dicarboxylic acids or hydroxyfatty alcohols or mixtures thereof. More particularly, they have been found to be caring, lighter and less greasy than comparable known compositions and leave the skin feeling dry rather than greasy while showing excellent skin-care properties.

The present invention also relates to the use of the wax dispersion according to the invention for the production of body care preparations. This is done by addition of the auxiliaries and additives typically encountered in cosmetic preparations and water.

Waxes are normally understood to be natural or synthetic substances and mixtures having the following properties: they have a solid to brittle hard consistency, are coarsely to finely crystalline, transparent to opaque and normally melt above 30° C. without decomposing. Even slightly above their melting point, they are low in viscosity and non-stringing and are very temperature-dependent in their consistency and solubility. Wax-like compositions or wax phases which are distinguished by a melting point above 25° C., i.e. which liquify completely only above 25° C., may be used in accordance with the invention. In other words, these wax-like compositions or wax phases may still contain a certain percentage of liquid constituents or relatively low-melting components.

The wax phase of the compositions according to the invention contain less than 10% by weight water, preferably less than 6% by weight water and more particularly less than 3% by weight water. In a particularly preferred embodiment, the wax phase is water-free. Water-free in the context of the invention means that the wax phase may have a small water content originating solely from its raw materials, but does not contain any added water. In the processing and application of the composition to the wipes, the wipes can thus be aftertreated with aqueous/surfactant-containing solutions without the wax dispersion dissolving. The water phase may contain water-soluble active components, for example urea and hydantoin, water-soluble or water-swellable polymers, humectants, etc.

The wax phase of the wax dispersions according to the invention may also be formulated exclusively from dialkyl (ene) ethers, dialkyl(ene) carbonates, dicarboxylic acids or hydroxyfatty alcohols or mixtures thereof with a wax-like consistency, but preferably contain other wax-like lipid components and oils according to the requirement profile. The melting range of the composition as a whole must be above 25° C. Accordingly, liquid dialkyl(ene) ethers, dialkyl(ene) carbonates, dicarboxylic acids or hydroxyfatty alcohols may also be used in accordance with the invention providing the wax phase has the required melting point of higher than 25° C. A preferred embodiment of the wax dispersion according to the invention contains a wax phase which melts in the range from 35 to 50° C., preferably in the range from 35 to 45° C. and more particularly in the range from 37 to 42° C. This ensures that, after coating of the wipes, the wax phase is present in the form of fine particles and only liquefies on application at body temperature. Tissues and wipes coated with such wax dispersions are particularly stable in storage and mixing of the phases is avoided. In addition, the fine-droplet wax phase only melts when the tissues are applied to the skin.

A particularly advantageous embodiment of the invention are wax dispersions which contain particles with an average particle size of 1 to 50 μm and more particularly 5 to 30 μm.

The dialkyl(ene) ethers may be symmetrical or nonsymmetrical, branched or unbranched, saturated or unsaturated. Dialkyl(ene) ethers particularly suitable for the purposes of the invention are wax-like saturated $C_{16-30}$ dialkyl ethers, more particularly $C_{16-24}$ dialkyl ethers. $C_{16-20}$ dialkyl ethers are particularly preferred, distearyl ether and dibehenyl ether being most particularly suitable. Relatively short-chain dialkyl ethers, for example di-n-octyl ether, di(2-ethylhexyl)-ether, lauryl methyl ether or octyl butyl ether, didoceyl ether, may also be used in accordance with the invention providing the wax phase has the required melting point. The dialkyl (ene) ethers can be produced from fatty alcohols in the presence of acidic catalysts by generally known methods, cf. for example DE 195 11 668 A1, DE 198 31 705 A1 and DE 199 43 585. Typical examples of such ethers are products obtained by etherification of caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadoleyl alcohol, behenyl alcohol, erucyl alcohol and brassidyl alcohol, Guerbet alcohols and the technical mixtures thereof obtained for example in the high-pressure hydrogenation of technical methylesters based on fats and oils. Dialkyl(ene) ethers solid at 25° C. are particularly suitable.

The dialkyl(ene) carbonates may be symmetrical or non-symmetrical, branched or unbranched, saturated or unsaturated. Among the dialkyl carbonates, wax-like, linear or branched, saturated or unsaturated $C_{14-30}$ dialkyl(ene) carbonates are preferred for the purposes of the invention. $C_{16-24}$ dialkyl(ene) carbonates are particularly preferred and, of these, saturated unbranched $C_{16-22}$ dialkyl carbonates are particularly suitable. Distearyl carbonate is most particularly preferred. However, liquid dialkyl(ene) carbonates such as, for example, dihexyl, dioctyl, di-(2-ethylhexyl) or dioleyl carbonate may also be used in accordance with the invention providing the wax phase of the wax dispersion has the required melting point. The compounds may be obtained by transesterification of dimethyl or diethyl carbonate with the corresponding hydroxy compounds by known methods. A relevant overview can be found in Chem. Rev. 96, 951 (1996). Typical examples of dialkyl(ene) carbonates are transesterification products of dimethyl and/or diethyl carbonate with caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadolelyl alcohol, behenyl alcohol, erucyl alcohol and brassidyl alcohol, Guerbet alcohols and the technical mixtures thereof obtained, for example, in the high-pressure hydrogenation of technical methyl esters based on fats and oils. Dialkyl(ene) carbonates solid are 25° C. are particularly suitable.

According to the invention, $C_{9-34}$ dicarboxylic acids may be used as the dicarboxylic acids. Such acids include, for example, octadecanedioic acid, tetratridecanoic acid, etc. According to the invention, azelaic acid—a $C_9$ dicarboxylic acid—is particularly suitable.

Among the hydroxyfatty alcohols, saturated or unsaturated, branched or unbranched compounds are suitable. $C_{12-30}$ fatty alcohols are preferred, the position of the hydroxy substituent being dependent upon the synthesis route and the educts used. Such fatty alcohols include, for example, decane-1,10-diol (Speziol® 10/2), hexanedecane-1,2-diol, 12-hydroxystearyl alcohol or hydroxyguerbet alcohols. According to the invention, hydroxyfatty alcohols solid at 25° C. are particularly suitable although liquid hydroxyfatty alcohols may also be used providing the wax phase has the required melting point. The 12-hydroxystearyl alcohol marketed by Cognis France S.A. under the name of Speziol® 18/2 is particularly preferred. Hexanecane-1,2-diol is obtained by ring opening of the corresponding α-epoxide.

The dialkyl ethers, dialkyl carbonates and dicarboxylic acids and hydroxyalcohols are present in a total quantity of preferably 1 to 30% by weight, more preferably 0.5 to 20% by weight and most preferably 0.5 to 10% by weight, based on the composition as a whole.

The compositions according to the invention are substantially odorless, ecotoxicologically safe and readily biodegradable. They are suitable as fat-containing, mild cosmetic preparations and may also be incorporated as a base in cosmetic personal hygiene and body care preparations, such as creams, lotions, sprayable emulsions, sun protection products, antiperspirants, etc. They may be applied as a care component to tissues, papers and wipes which are used in the field of hygiene and care (wet wipes for baby hygiene and baby care, cleaning wipes, facial wipes, skin care wipes, wipes containing active components against skin ageing, wipes containing sun protection formulations and insect repellents and wipes for decorative cosmetics or for aftersun treatment, wet toilet wipes, antiperspirant wipes).

Emulsifiers

The addition of the emulsifiers increase the stability of the fine-droplet wax dispersion. Suitable emulsifiers are ionic and nonionic emulsifiers, nonionic emulsifiers being preferred for the purposes of the invention. In addition, small quantities of water-soluble substances and active components, water and humectants may be incorporated.

The nonionic emulsifiers present in a preferred embodiment of the invention are distinguished by their dermatological compatibility and mildness and by their ecotoxicologically favorable properties. In addition, they are particularly suitable for stabilizing the fine-droplet wax dispersion. Compositions with improved stability are obtained by using a combination of nonionic w/o and o/w emulsifiers. The wax dispersions according to the invention contain the emulsifier(s) in a quantity of 0.1 to 10% by weight, preferably 0.5 to 7% by weight and more particularly 1 to 5% by weight, based on the total weight of the wax dispersion.

Nonionic Emulsifiers

The group of nonionic emulsifiers includes, for example, (1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12/18}$ fatty acid monoesters and diesters of addition products of 1 to 50 mol ethylene oxide onto glycerol;
(3) ethylene oxide addition products of glycerol mono- and diesters; sorbitan mono- and diesters of saturated and unsaturated fatty acids containing 6 to 22 carbon atoms and ethylene oxide addition products thereof;
(4) alkyl mono- and oligoglycosides containing 8 to 22 carbon atoms in the alkyl group and ethoxylated analogs thereof;
(5) addition products of 7 to 60 mol ethylene oxide onto castor oil and/or hydrogenated castor oil;
(6) polyol esters and, in particular, polyglycerol esters such as, for example, polyol poly-12-hydroxystearates, polyglycerol polyricinoleate, polyglycerol diisostearate or polyglycerol dimerate. Mixtures of compounds from several of these classes are also suitable;
(7) addition products of 2 to 15 mol ethylene oxide onto castor oil and/or hydrogenated castor oil;
(8) partial esters based on linear, branched, unsaturated or saturated $C_{6-22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters, such as glyceryl stearate citrate and glyceryl stearate lactate for example;
(9) polysiloxane/polyalkyl/polyether copolymers and corresponding derivatives;
(10) mixed esters of pentaerythritol, fatty acids, citric acid and fatty alcohol and/or mixed esters of $C_{6-22}$ fatty acids, methyl glucose and polyols, preferably glycerol or polyglycerol;
(11) polyalkylene glycols.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. These emulsifiers are w/o or o/w emulsifiers, depending on the degree of ethoxylation. $C_{12/18}$ fatty acid monoesters and diesters of addition products of ethylene oxide onto glycerol are known as lipid layer enhancers for cosmetic preparations.

According to the invention, particularly suitable and mild emulsifiers are the polyol poly-12-hydroxystearates and mixtures thereof marketed by Cognis Deutschland GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier), cf. in particular EP 0 766 661 B1. The polyol component of these emulsifiers may be derived from substances which contain at least two, preferably 3 to 12 and more particularly 3 to 8 hydroxyl groups and 2 to 12 carbon atoms.

In principle, suitable lipophilic w/o emulsifiers are emulsifiers with an HLB value of 1 to 8 which are listed in numerous Tables and are well-known to the expert. Some of these emulsifiers are listed, for example, in Kirk-Othmer, "Encyclopedia of Chemical Technology", 3rd Edition, 1979, Vol. 8, page 913. The HLB value for ethoxylated products may also be calculated to the following formula: HLB=(100−L): 5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, such as for example partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. The corresponding addition products of ethylene oxide are also suitable emulsifiers.

In cases where water-soluble active components and/or small quantities of water are incorporated, it can also be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example 10-20 ethylene oxide units for o/w emulsifiers and 20-40 ethylene oxide units for so-called solubilizers. Particularly advantageous o/w emulsifiers for the purposes of the invention are Ceteareth-12 and PEG-20 Stearate. Particularly suitable solubilizers are Eumulgin® HRE 40 (INCI name: PEG-40 Hydrogenated Castor oil), Eumulgin® HRE 60 (INCI name: PEG-60 Hydrogenated Castor Oil), Eumulgin® L (INCI name: PPG-1-PEG-9 Laurylglycolether) and Eumulgin® SML 20 (INCI name: Polysorbat-20).

Nonionic emulsifiers from the group of alkyl oligoglycosides are particularly compatible with the skin and are therefore particularly suitable as o/w emulsifiers. $C_{8-22}$ alkyl mono- and oligoglycosides, their production and their use are known from the prior art. They are produced in particular by reacting glucose or oligosaccharides with primary alcohols containing 8 to 22 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based. Products available under the name of Plantacare® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68/50 by Cognis Deutschland GmbH, which is a 1:1 mixture of alkyl polyglucosides and fatty alcohols, is preferred for the purposes of the invention. According to the invention, the mixture of Lauryl Glucoside, Polyglyceryl-2-Dipolyhydroxystearate, glycerol and water which is marketed as Eumulgin®) VL 75 may also be used with advantage in accordance with the invention.

Other Surfactants/Emulsifiers

The wax dispersions according to the invention may additionally contain anionic, zwitterionic, amphoteric or cationic surfactants according to the application envisaged for the wipes and tissues.

The addition of anionic surfactants/emulsifiers to the wax dispersion is also suitable for the purposes of the invention. Anionic surfactants are characterized by a water-solubilizing anionic group, such as for example a carboxylate, sulfate, sulfonate or phosphate group, and a lipophilic residue. Dermatologically compatible anionic surfactants are known to the expert in large numbers from relevant manuals and are commercially available. More particularly, they are alkyl sulfates in the form of their alkali metal, ammonium or alkanolammonium salts, alkyl ether sulfates, alkyl ether carboxylates, acyl isethionates, acyl sarcosinates, acyl taurines with linear $C_{12-18}$ alkyl or acyl groups and sulfosuccinates and acyl glutamates in the form of their alkali metal or ammonium salts.

Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the INCI name of Cocamidopropyl Betaine is a particularly preferred zwitterionic surfactant.

Ampholytic surfactants are also suitable, particularly as co-surfactants. Ampholytic surfactants are surface-active compounds which, in addition to a $C_{8/18}$ alkyl or acyl group, contain at least one free amino group and at least one $—COOH$ or $—SO_3H$ group in the molecule and which are capable of forming inner salts. Examples of suitable ampholytic surfactants are N-alkyl glycines, N-alkyl propionic acids, N-alkylamino-butyric acids, N-alkyliminodipropionic acids, N-hydroxyethyl-N-alkyl-amidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions according to the invention with particular softness. They are known substances which are prepared by the relevant methods of organic chemistry. Other cationic surfactants suitable for use in accordance with the invention are the quaternized protein hydrolyzates.

Other Wax-Like Lipid Components

In another preferred embodiment, the wax phases of the wax dispersion contain at least one other wax-like lipid component. Through the addition of other wax-like lipid components, the sensory properties and the stability of the wax dispersion can be further optimized and adapted to the requirement profile. "Wax-like" compounds are compounds of wax-like consistency (see above) with a melting point above 25° C.

According to the invention, any fats and fat-like substances with a wax-like consistency may be used as other lipid components (for a definition, see CD Römpp Chemie Lexikon—Version 1.0., Stuttgart/New York: Georg Thieme Verlag 1995). These include inter alia fats (triglycerides), mono- and diglycerides, waxes, fatty and wax alcohols, fatty acids, esters of fatty alcohols and fatty acid amides or mixtures of these substances. They may be present in the compositions according to the invention in a total quantity of 0.1 to 45% by weight, preferably 5 to 30% by weight and more particularly 10 to 25% by weight, based on the wax dispersion as a whole.

Fats

Fats in the context of the invention are understood to be triacylglycerols, i.e. the triple esters of fatty acids with glycerol. Among the triacylglycerols, those which melt at 35 to 50° C., preferably at 35 to 45° C. and more particularly at 37 to 42° C. are preferred as the lipid component. They preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Gycerol tristearate, glycerol tribehenate (for example Syncrowax® HRC), glycerol tripalmitate or the triglyceride mixtures known under the name of Syncrowax® HGLC, are also suitable providing the melting point of the wax phase is above 25° C. and preferably in the range from 35 to 50° C.

Besides the triglycerides, other suitable lipid components are mono- and diglycerides and mixtures of glycerides. According to the invention, preferred glyceride mixtures include the products Novata® AB and Novata® B (mixture of $C_{12-18}$ mono-, di- and triglycerides) and Cutina® MD or Cutina® GMS (glyceryl stearate) marketed by Cognis Deutschland GmbH & Co. KG. The glyceride (mixture) may be present in a quantity of 0.1 to 45% by weight, preferably in a quantity of 0.1 to 15% by weight and more particularly in a quantity of 1 to 12% by weight, based on the wax dispersion.

Mixed esters and mixtures of mono-, di- and triglycerides are particularly suitable for the purposes of the invention because they have a relatively low tendency towards crystallization and thus improve the performance of the composition according to the invention.

Fatty Alcohols and Fatty Acids

Fatty alcohols with a wax-like consistency suitable for use in accordance with the invention include $C_{12-60}$ fatty alcohols, more particularly $C_{12-24}$ fatty alcohols obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol and wax-like Guerbet alcohols. According to the invention, saturated, branched or unbranched fatty alcohols are preferred. Other suitable fatty alcohols are the wax-like fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, wax-like synthetic alcohols, for example the linear, even-numbered fatty alcohols from Ziegler's synthesis (Alfols®) or the partly branched alcohols from the oxosynthesis (Dobanols®) may also be used. The $C_{14-18}$ fatty alcohols marketed for example by Cognis Deutschland GmbH & Co. KG under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are suitable for the purposes of the invention. Fatty alcohols give the compositions a dryer feeling on the skin than triglycerides and are therefore preferably used. The fatty alcohol(s) may be present in a quantity of 0.1 to 45% by weight, preferably in a quantity of 1 to 25% by weight and more particularly in a quantity of 5 to 20% by weight, based on the wax dispersion.

$C_{14-40}$ fatty acids or mixtures thereof may be used as additional wax-like lipid components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes

Other waxes suitable for use as an additional lipid component in accordance with the present invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Wax components such as these include, for example, $C_{16-40}$ alkyl stearates, $C_{20-40}$ alkyl stearates (for example Kesterwachs®) K82H), $C_{20-40}$ dialkyl esters of dimer acids, $C_{18-38}$ alkyl hydroxystearoyl stearates or $C_{20-40}$ alkyl erucates. Other suitable wax components which may be used with advantage are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate. Myristyl lactate (Cegesoft® C17) inter alia is particularly suitable for skin-care wipes because it binds well to the skin. Silicone waxes may also be used with advantage.

In a preferred embodiment of the invention, at least one other lipid component selected from $C_{12-24}$ fatty alcohols, the mono-, di- or triesters of glycerol and $C_{12-24}$ fatty acids, the mono- or diesters of ethylene glycol and $C_{12-24}$ fatty acids or a mixture thereof is present. A $C_{12-24}$ fatty alcohol or a combination of at least one $C_{12-24}$ fatty alcohol with mono- or diesters of glycerol or ethylene glycol and $C_{12-24}$ fatty acids is particularly preferred for the purposes of the invention.

Small quantities of alkali metal and alkaline earth metal and aluminium salts of $C_{12-24}$ fatty acids or $C_{12-24}$ hydroxyfatty acids may optionally be used as additional consistency factors, calcium, magnesium, aluminium and, in particular, zinc stearate being preferred.

Oil Components

In another preferred embodiment, the composition according to the invention contains at least one oil component. In the context of the invention, oil components are substances or mixtures of substances which are liquid at 20° C. and immiscible with water at 25° C. Such substances include any oil components which are not among the dialkyl(ene) ethers, dialkyl(ene) carbonates, dicarboxylic acids or hydroxyfatty alcohols mentioned in claim 1, i.e. for example glycerides, hydrocarbons, silicone oils, ester oils liquid at 20° C. or mixtures thereof. The oil components are present in the compositions according to the invention in quantities of normally less than 30% by weight, preferably in quantities of 0.5 to 10% by weight and more particularly in quantities of 0.5 to 5% by weight, based on the wax dispersion. The quantity of oils incorporated is limited by the proviso that the melting point of the wax phase must be above 25° C. Such optimizations are among the routine optimizations of the expert.

Glycerides suitable as oil components in accordance with the invention include fatty acid esters of glycerol liquid at 20° C. which may be of natural (animal and vegetable) or synthetic origin. Glycerides are divided into mono-, di- and triglycerides. They are known substances which may be obtained by the relevant methods of preparative organic chemistry. Synthetic glycerides are normally mixtures of mono-, di and triglycerides which are obtained by transesterification of the corresponding triglycerides with glycerol or by selective esterification of fatty acids. Preferred fatty acids for the purposes of the invention are $C_{6-24}$ fatty acids and, among these, $C_{6-18}$ fatty acids and especially $C_{8-18}$ fatty acids. The fatty acids may be branched or unbranched, saturated or unsaturated. According to the invention, it is preferred to use glycerides of vegetable origin liquid at 20° C., more particularly cocoglycerides, a mixture of predominantly di- and triglycerides with $C_{8-18}$ fatty acids marketed under the name of Myritol® 331 by Cognis Deutschland GmbH. It is also preferred to use Myritol® 312 ($C_{8/10}$ triglycerides), Cegesoft® PS 17, Cegesoft® GPO, Cegesoft® PFO and Cegesoft® PS 6 which give the compositions particularly favorable care properties after application.

Other suitable oil components are Guerbet alcohols liquid at 20° C. based on fatty alcohols containing 6 to 18 and preferably 8 to 10 carbon atoms, such as Eutanol® G for example. Liquid esters of linear, saturated or unsaturated $C_{6-22}$ fatty acids with linear or branched, saturated or unsaturated $C_{6-22}$ fatty alcohols or esters of branched $C_{6-13}$ carboxylic acids with linear or branched, saturated or unsaturated $C_{6-22}$ fatty alcohols may also be used as oil components in accordance with the invention.

Examples of liquid wax esters include the following typical representatives: decyl oleate (Cetiol® V), cococaprylate/caprate (Cetiol® SN), hexyl laurate (Cetiol® A), myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate (Cetiol® J 600), behenyl isostearate, erucyl isostearate, erucyl oleate. Also suitable are esters of linear $C_{6-22}$ fatty acids with branched alcohols, more particularly 2-ethyl hexanol (Cetiol® 868), esters of branched $C_{6-22}$ fatty acids with linear alcohols, esters of $C_{18-38}$ alkylhydroxy-carboxylic acids with linear or branched $C_{2-12}$ fatty alcohols, esters of linear and/or branched fatty acids with polyhydric alcohols (for example propylene glycol, dimer diol or trimer triol) and/or Guerbet alcohols and esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms (for example Dioctyl Malate).

Other oil components suitable for use in accordance with the invention are natural and synthetic, aliphatic and/or naphthenic hydrocarbons liquid at 20° C., such as for example squalane, squalene, paraffin oils, isohexadecane, isoeicosane or polydecenes and dialkyl cyclohexanes (Cetiol®).

According to the invention, other suitable oil components are liquid silicone oils. These include, for example, dialkyl and alkylaryl siloxanes, such as for example cyclomethicone, dimethyl polysiloxane and methylphenyl polysiloxane and alkoxylated and quaternized analogs thereof. Suitable non-volatile silicone oils are, for example, polyalkyl siloxanes, polyalkylaryl siloxanes and polyether siloxane copolymers. The addition of silicone compounds imparts a particularly light feeling on the skin.

In a preferred embodiment, the wax dispersion according to the invention contains 1 to 50% by weight of a wax phase comprising (a1) 0.1 to 30% by weight of at least one oil or wax component selected from $C_{14-30}$ dialkyl(ene) ethers, $C_{14-30}$ dialkyl (ene) carbonates, $C_{9-34}$ dicarboxylic acids or $C_{12-30}$ hydroxyfatty alcohols or a mixture of these substances, (a2) 0.1 to 10% by weight of at least one oil, (a3) 0.1 to 10% by weight of at least one nonionic emulsifier, (a4) 0.1 to 40% by weight of at least one other wax-like lipid component, based on the overall composition of the wax dispersion, and (b) 50 to 99% by weight of a water phase, based on the overall composition of the wax dispersion.

Polymers

In another preferred embodiment, the composition according to the invention contains at least one polymers, preferably in the water phase. The polymer contributes towards further improving the particle fineness of the dispersion. The polymers are preferably present in a quantity of 0.01 to 5% by weight, more preferably in a quantity of 0.05 to 3% by weight and most preferably in a quantity of 0.1 to 2% by weight, based on the wax dispersion.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Polysaccharides, more especially xanthan gum, guar guar, agar agar, alginates and tyloses, carboxymethyl cellulose and hydroxyethyl cellulose, polyacrylates (for example Carbopols® from Noveon or Synthalens® from 3v/Sigma), polyacrylamides, polyvinyl alcohol and relatively high molecular weight polyethylene glycol mono- and diesters of fatty acids are suitable for the purposes of the invention.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grunau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 from Celanese, quaternized ammonium salt polymers such as, for example, Mirapol® A-15, Mirapol® AD-1, Mirapol® AZ-1 from Miranol.

Polymers soluble in or swellable with water, more particularly nonionic and anionic polymers, are preferred for the purposes of the invention. Polymers selected from the group consisting of polyacrylates, polysaccharides, polyacrylamides or a mixtures thereof are particularly preferred.

Active Components

A preferred embodiment of the composition according to the invention additionally contains at least one active component. In the context of the invention, active components are understood to be substances which contribute towards protecting the skin and strengthening the skin barrier and have an irritation-soothing, antimicrobial or skin-moisturizing effect. Preferred active components according to the invention are those which soothe inflammatory skin processes or reddened, sore skin, including for example zinc compounds and sulfur. The active component is present in a quantity of normally 0.01 to 10% by weight, preferably 0.1 to 7% by weight and more particularly 1 to 5% by weight, according to type. Oil-soluble active components are preferred for the purposes of the invention although limited quantities of water-soluble active components may also be incorporated through the addition of emulsifiers and/or solubilizers. The active components may also be present in combination with one another.

Also suitable are plant extracts which often contain a synergistic combination of wound-healing/irritation-soothing substances. These extracts are normally obtained by extraction of the whole plant. In individual cases, however, it can also be preferred to prepare the extracts exclusively from flowers and/or leaves of the plant.

According to the invention, the extracts of, above all, chamomile, aloe vera, hamamelis, lime blossom, horse chestnut, green tea, oak bark, stinging nettle, hops, burdock root, horse willow, hawthorn, almond, pine needle, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root are suitable.

Suitable extractants for the preparation of the plant extracts mentioned are water, alcohols and mixtures thereof. Among the alcohols, lower alcohols, such as ethanol and isopropanol, but especially polyhydric alcohols, such as ethylene glycol and propylene glycol, are preferably used both as sole extractant and in the form of mixtures with water. Plant extracts based on water/propylene glycol in a ratio of 1:10 to 10:1 have proved to be particularly suitable.

Antimicrobial/Biogenic Active Components

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. An interesting natural deodorant is the terpene alcohol farnesol (3,7,11-trimethyl-2,6,10-dodecatrien-1-ol) which is present in lime blossom oil and which smells of lily-of-the-valley. Glycerol monolaurate, glycerol stearate, glycerol oleate and glycerol diolate have also been found to show germ-inhibiting activity and, by virtue of their particular mildness and harmlessness, may be used with particular advantage in baby hygiene and baby care. In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, α-hydroxycarboxylic acids, amino acids, ceramides, pseudo-ceramides, essential oils, plant extracts and vitamin complexes. According to the invention, preferred active components are oil-soluble vitamins and vitamin precursors. Tocopherol (vitamin E) and tocopherol derivatives are most particularly preferred.

The percentage content of germ inhibitors is normally about 0.1 to 2% by weight, based on the wax dispersion. The glycerol esters may be used in relatively large quantities (vide supra).

Humectants/Skin Moisturizers

In another preferred embodiment, the composition according to the invention also contains at least one humectant. This active component contributes towards improving the sensory properties of the composition and serves to regulate the skin moisture level. In addition, it can contribute towards improving the penetration behavior of the composition on the wipes. The humectants are normally present in a quantity of 0.1 to 10% by weight, preferably 0.5 to 10% by weight and more particularly 0.5 to 5% by weight, based on the wax dispersion.

According to the invention, suitable humectants are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol and triglycerol.

Process

The present invention also relates to a process for the production of a wax dispersion with an average particle size of 0.5 to 100 μm, characterized in that a preliminary emulsion of the wax phase containing a water phase is prepared and the resulting hot preliminary emulsion, which has a temperature above the melting range of the waxes (typically above 40-90°

C.), is introduced into a cold polymer-containing water phase which has a temperature of 1 to 30° C. The temperature of the water phase is preferably 25° C. or lower, a temperature of 5 to 25° C. being particularly preferred. The temperature of this cold water phase should not reach the melting range of the waxes used during addition of the "warmer" preliminary emulsion and should therefore be cooled accordingly. The wax components may be selected from any of the above-mentioned wax components.

The polymer is preferably soluble in or swellable with water. The polymers make it possible to obtain very fine-droplet and stable wax dispersions which do not separate, even in the event of prolonged storage. In a preferred embodiment, the preliminary emulsion also contains a polymer. Suitable polymers have already been described (vide supra). In another preferred embodiment of the process, the polymer is selected from the group consisting of polyacrylates, polysaccharides, polyacrylamides or a mixture of these substances.

The "hot" preliminary emulsion is introduced into the "cold" water phase by any of the usual methods well-known to the expert. In order to obtain particularly fine droplets, the preliminary emulsion is preferably homogenized at least once before it is introduced into the water phase. The homogenization may be carried out, for example, as high-pressure homogenization. In another preferred embodiment, the preliminary emulsion is coooled in a heat exchanger, preferably to temperatures below 50° C., before introduction into the water phase. The preliminary emulsion is preferably sprayed under pressure into the water phase through a nozzle. The exact pressure conditions are adjusted according to the particular apparatus.

In another preferred embodiment of the process, the wax phase contains at least one oil or wax component selected from dialkyl(ene) ethers, dialkyl(ene) carbonates, dicarboxylic acids or hydroxyfatty alcohols or a mixture of these substances and at least one emulsifier. These substances were also disclosed in detail at the beginning. The melting point of the waxes is preferably above 25° C.

According to the invention, the quantities used are preferably selected so that the proces according to the invention gives wax dispersions which contain (a) 1 to 75% by weight of a wax phase and (b) 25 to 99% by weight of a water phase, based on the overall composition.

Other Auxiliaries and Additives

The compositions according to the invention may contain a number of other auxiliaries and additives depending on their intended application, including for example superfatting agents, other thickeners, powders, biogenic agents, deodorants, film formers, UV protection factors, antioxidants, hydrotropes, preservatives, insect repellents, self-tanning agents, solubilizers, perfume oils, dyes and the like.

Preferred UV protection factors (for example for sunscreen wipes) are derivatives of benzophenone, for example 2-hydroxy-4-methoxybenzophenone, 2-hydroxy-4-methoxy-4'-methylbenzophenone and/or 2,2'-dihydroxy-4-methoxybenzophenone.

Preferred antioxidants are carotinoids, carotenes (for example α-carotene, β-carotene, lycopene) and derivatives thereof, α-hydroxy acids (for example citric acid, lactic acid, malic acid), EDTA, vitamin C and derivatives (for example ascorbyl palmitate, Mg ascorbyl phosphate, ascorbyl acetate), tocopherols and derivatives (for example viutamin E acetate), butyl hydroxytoluene and butyl hydroxyanisole.

EXAMPLES

Production Process
Production of the Wax Dispersion in a 1,000 kg Plant:

Distearyl carbonate (20 kg), distearyl ether (20 kg), Lorol® $C_{12}$ (50 kg), Lanette® 14 (20 kg), Lanette® 16 (20 kg), Lanette® 18 (10 kg), paraffin oil perl. DAB (20 kg), part of the emulsifier Eumulgin® B2 (3.0 kg), Dehymuls® PGPH (1.0 kg), part of the polymer Sepigel® 305 (1.0 kg) and part of the deionized water (430.0 kg) were introduced into a heatable stirred tank reactor 1 (3 m³). The reactor was then heated to temperatures above the melting temperature of the waxes used (in this case ca. 80-90° C.) and vigorously stirred (propeller stirrer at ca. 200 r.p.m.) until a homogeneously dispersed preliminary emulsion was obtained. The preliminary emulsion was then passed from the stirred tank reactor 1 through a Supraton® homogenizer via a centrifugal pump which generates an approximate pressure of 2 bar. The preliminary emulsion was first circulated for ca. 30 minutes, i.e. after the centrifugal pump, it was pumped through the Supraton® homogenizer (manufacturer: Supraton) and then back into the stirred tank reactor 1. After the 30-minute circulation, the preliminary emulsion was then pumped from the Supraton® through a plate-type heat exchanger (W. Schmidt GmbH) rather than back into the stirred tank reactor 1. The plate-type heat exchanger was cooled via a cold water circuit (ca. 7° C.). In this way, the homogenized preliminary emulsion was cooled to ca. 50° via the plate-type heat exchanger and then introduced into the stirred tank reactor 2 under an approximate pressure of 2 bar. The preliminary emulsion was introduced into the stirred tank reactor through a nozzle located below the liquid level, i.e. without allowing air to be introduced.

The remaining deionized water (396.0 kg), the rest of the dissolved nonionic emulsifier Eumulgin® B2 (1.0 kg) and the polymer Sepigel® 305 (3.0 kg) were introduced into stirred tank reactor 2 (1 m³), i.e. the collecting vessel, and cooled to around 5° C. The preliminary emulsion has to be added with efficient stirring (propeller stirrer, ca. 120 r.p.m.) and with external jacket cooling of the stirred tank reactor 2, so that a temperature below 25° C. was guaranteed for introduction of the preliminary emulsion. Phenoxyethanol (5.0 kg) was then added with vigorous stirring as a preservative.

The viscosity of this wax dispersion, as measured with a Brookfield RVF, spindle 5, 10 r.p.m., was 30,000 mPa·s at 23° C. Particle size measurement was carried out by Fraunhofer diffraction (Mastersizer 2000, Malvern Instruments Ltd.) and produced a particle size distribution d(0.5) of 10 micrometers and d(0.9) of 30 micrometers, i.e. 50% of the dispersed material was smaller than 10 micrometers and 90% smaller than 30 micrometers.

To assess its performance properties, the composition according to the invention was stability-tested and its sensory properties evaluated. Commercially available wipes (substrate) weighing 55 g/m² were coated with the wax dispersions according to the invention in a quantity of 165 g/m². The compositions according to the invention can be applied more advantageously than known compositions and are superior to known compositions in regard to sensory properties and storage stability.

The quantities mentioned in the following Examples are based on % by weight of the commercially available substances in the composition as a whole (wax dispersion), unless otherwise indicated. Examples 1 to 5 are formulations corresponding to the invention; C1 is a Comparison Example.

TABLE 1

(wax dispersions)

| Ingredients | Ex. 1 % by wt. | Ex. 2 % by wt. | Ex. 3 % by wt. | Ex. 4 % by wt. | Ex. 5 % by wt. | C 1 % by wt. |
|---|---|---|---|---|---|---|
| Distearyl Carbonate | 3.0 | — | 2.5 | — | 1.0 | — |
| Distearyl Ether | — | 2.0 | 2.5 | — | — | — |
| Dibehenyl Ether | — | 1.0 | — | — | — | — |
| Azelaic acid | 2.0 | — | — | 1.0 | 1.0 | — |
| 12-Hydroxystearyl alcohol | — | 4.0 | — | 2.5 | — | — |
| Lorol ® C12 | 3.0 | 2.0 | 3.0 | 4.0 | 1.0 | 2.0 |
| Lanette ® 14 | 2.0 | 2.0 | 3.0 | 2.0 | 1.0 | 4.0 |
| Lanette ® 16 | 2.0 | 3.0 | 4.0 | 3.0 | 0.5 | 3.0 |
| Lanette ® 18 | 0.5 | 1.0 | 1.0 | — | 0.5 | 2.0 |
| Lanette ® O | — | — | — | 2.0 | — | — |
| Cutina ® MD | — | 2.0 | — | — | 1.0 | — |
| Cutina ® AGS | — | — | 2.0 | — | — | — |
| Novata ® B | — | — | 0.5 | 5.0 | 3.0 | — |
| Cegesoft ® HF 52 | — | — | — | 1.0 | 2.0 | — |
| Cegesoft ® SH | — | — | — | — | 5.0 | — |
| Emulgade ® PL 68/50 | 0.5 | — | — | 1.0 | 2.0 | 0.5 |
| Eumulgin ® VL 75 | — | — | 1.0 | — | — | — |
| Eumulgin ® B1 | — | 2.0 | 0.2 | 0.5 | — | — |
| Eumulgin ® B2 | 0.5 | — | — | — | — | — |
| Lanette ® E | — | — | — | 0.1 | — | — |
| Dehymuls ® PGPH | — | 0.2 | 0.2 | — | — | — |
| Cetiol ® 868 | 0.5 | — | 1.0 | — | 1.0 | 0.5 |
| Cetiol ® OE | — | 1.0 | 0.5 | — | — | — |
| Mineral oil (Klearol) | — | 0.5 | — | — | — | — |
| Cegesoft ® PS 6 | — | — | — | 1.0 | — | — |
| Cetiol ® CC | 1.0 | — | — | 1.0 | — | 1.0 |
| Myritol ® 331 | — | 0.2 | 0.5 | 0.5 | — | — |
| Natrosol ® 250 HR | 0.2 | — | — | — | — | — |
| Hispagel ® 200 | — | 3.0 | 1.0 | — | — | — |
| Jaguar ® HP-105 | — | — | — | 0.4 | — | — |
| Cosmedia ® SP | — | 0.3 | — | — | 0.3 | — |
| Sepigel ® 305 | 0.2 | — | 0.4 | — | — | — |
| Panthenol | 1.0 | — | — | — | — | 1.0 |
| Butylene Glycol | — | — | — | 1.0 | — | — |
| Copherol ® F1300 | — | — | — | 0.5 | — | — |
| Neo Heliopan, Type BB | — | — | — | 0.5 | — | — |
| Glycerin | — | — | 1.0 | — | 2.0 | — |
| Bisabolol | — | 0.5 | — | — | — | — |
| Hibiscin ® HP LS 9198) | — | — | 1.0 | — | — | — |
| Preservative | qs | qs | qs | qs | qs | qs |
| Water, demineralized | to 100 | to 100 | to 100 | to 100 | to 100 | to 100 |
| Particle fineness/stability of the dispersion | + | + | + | + | + | − |

APPENDIX

1) Cegesoft® HF 52
   INCI: Hydrogenated Vegetable Oil
   Manufacturer: Cognis Deutschland GmbH & Co. KG
2) Cegesoft® PS 6
   INCI: Vegetable Oil
   Manufacturer: Cognis Deutschland GmbH & Co. KG
3) Cegesoft® SH
   INCI: Shorea Stenoptera
   Manufacturer: Cognis Deutschland GmbH & Co. KG
4) Cetiol® CC
   INCI: Dicaprylyl Carbonate
   Manufacturer: Cognis Deutschland GmbH & Co. KG
5) Cetiol® OE
   INCI: Dicaprylyl Ether
   Manufacturer: Cognis Deutschland GmbH & Co. KG
6) Cetiol® 868
   INCI: Octyl Stearate
   Manufacturer: Cognis Deutschland GmbH & Co. KG
7) Copherol® F 1300
   INCI: Tocopherol
   Manufacturer: Cognis Deutschland GmbH & Co. KG
8) Cosmedia® SP
   INCI: Sodium Polyacrylate
   Manufacturer: Cognis Deutschland GmbH & Co. KG
9) Cutina® AGS
   INCI: Glycol Distearate
   Manufacturer: Cognis Deutschland GmbH & Co. KG
10) Cutina® MD
    INCI: Glyceryl Stearate
    Manufacturer: Cognis Deutschland GmbH & Co. KG
11) Dehymuls® PGPH
    INCI: Polyglyceryl-2 Dipolyhydroxystearate
    Manufacturer: Cognis Deutschland GmbH & Co. KG
12) Emulgade® PL 68/50
    INCI: Cetearyl Glucoside, Cetearyl Alcohol
    Manufacturer: Cognis Deutschland GmbH & Co. KG
13) Eumulgin® B1
    INCI: Ceteareth-12
    Manufacturer: Cognis Deutschland GmbH & Co. KG
14) Eumulgin® B2
    INCI: Ceteareth-20
    Manufacturer: Cognis Deutschland GmbH & Co. KG 15) Eumlugin® VL75
   INCI: Lauryl Glucoside, Polyglyceryl-2 Dipolyhydroxystearate, Glycerin,
      Aqua (Water); ca. 75% Aktivsubstanz in Wasser
   Manufacturer: Cognis Deutschland GmbH & Co. KG
16) Hibiscin® HP LS 9198
   INCI: Water and Hibiscus esculentus seed extract
   Manufacturer: Laboratoires Serobiologiques
17) Hispagel® 200
   INCI: Glycerin, Glyceryl Polyacrylate
   Manufacturer: Cognis Iberia
18) Jaguar HP-105
   INCI: Hydroxypropyl Guar
   Manufacturer: Rhodia
19) Lanette® 14
   INCI: Myristyl Alcohol
   Manufacturer: Cognis Deutschland GmbH & Co. KG
20) Lanette® 16
   INCI: Cetyl Alcohol
   Manufacturer: Cognis Deutschland GmbH & Co. KG
21) Lanette® 18
   INCI: Stearyl Alcohol
   Manufacturer: Cognis Deutschland GmbH & Co. KG
22) Lanette E
   INCI: Sodium Cetearyl Sulfate
   Manufacturer: Cognis Deutschland GmbH & Co. KG
23) Lanette® O
   INCI: Cetearyl Alcohol
   Manufacturer: Cognis Deutschland GmbH & Co. KG
24) Lorol C12
   INCI: Lauryl Alcohol
   Manufacturer: Cognis Deutschland GmbH & Co. KG
25) Myritol® 331
   INCI: Cocoglycerides
   Manufacturer: Cognis Deutschland GmbH & Co. KG
26) Natrosol® 250 HR
   INCI: Hydroxyethylcellulose
   Manufacturer: Hercules Inc.
27) Neo Heliopan, Type BB
   INCI: Benzophenone-3
   Manufacturer: Haarman & Reimer GmbH
28) Novata® B
   INCI: Cocoglycerides
   Manufacturer: Cognis Deutschland GmbH & Co. KG
29) Sepigel® 305
   INCI: Polyacrylamide, C13-C14 Isoparaffin, Laureth-7
   Manufacturer: SEPPIC

What is claimed is:

1. A wax dispersion having a particle size distribution such that 50% of the dispersed wax is <10 micrometers (μm), comprising:
   (a) 10% to 75% by weight, based on the dispersion, of a wax phase with a melting point in the range of from above 25° C. to about 50° C., which comprises at least one oil or wax component selected from the group consisting of dialkyl(ene) carbonates, dicarboxylic acids, hydroxyfatty alcohols, and mixtures thereof, and at least one emulsifier; and
   (b) a water phase.

2. The wax dispersion according to claim 1, wherein the at least one emulsifier of the wax phase is selected from the group of nonionic emulsifiers.

3. The wax dispersion according to claim 1, wherein the average particle size is 5 to 50 μm.

4. The wax dispersion according to claim 1, wherein the wax phase comprises less than 3% by weight of water, based on the total weight of the wax phase.

5. The wax dispersion according to claim 1, wherein the wax phase contains at least one further component selected form the group consisting of an other wax-like lipid component and an other oil component.

6. The wax dispersion according to claim 5, wherein the other wax-like lipid component is selected from the group consisting of $C_{12-24}$ fatty alcohols, mono-, di- or triesters of glycerol, $C_{12-24}$ fatty acids, mono- or diesters of ethylene glycol, $C_{12-24}$ fatty acids, and mixtures thereof.

7. The wax dispersion according to claim 1, further comprising at least one polymer.

8. The wax dispersion according to claim 7, wherein the polymer is selected from the group consisting of polyacrylates, polysaccharides, polyacrylamides, and mixtures thereof.

9. The wax dispersion according to claim 1, wherein the wax phase further comprises at least one active component.

10. The wax dispersion according to claim 1, further comprising at least one humectant.

11. A body care preparation comprising a wax dispersion according to claim 1.

12. A wax dispersion having a particle size distribution such that 50% of the dispersed wax is <10 micrometers (μm) comprising:
   (a) 10-25% by weight, based on the wax dispersion, of a wax phase with a melting point in the range of about 35 to about 50° C. which comprises:
      (1) at least one oil or wax component selected from $C_{14-30}$ dialkyl(ene) carbonates, $C_{9-34}$ dicarboxylic acids or $C_{12-30}$ hydroxyfatty alcohols, and mixtures thereof,
      (2) at least one other oil,
      (3) at least one nonionic emulsifier, and
      (4) at least one other wax-like lipid component; and
   (b) 75-90% by weight, based on the wax dispersion, of a water phase.

13. The wax dispersion according to claim 12, further comprising 0.01 to 5.0% by weight of at least one polymer, based on the overall wax dispersion.

14. The wax dispersion according to claim 13, wherein the polymer is selected from the group consisting of polyacrylates, polysaccharides, polyacrylamides, and mixtures thereof.

15. The wax dispersion according to claim 12, wherein the average particle size is 5 to 50 μm.

16. The wax dispersion according to claim 12, wherein the wax phase comprises less than 3% by weight, based on the weight of the wax phase, of water.

17. The wax dispersion according to claim 12, wherein the wax phase further comprises at least one active component.

18. The wax dispersion according to claim 12, further comprising at least one humectant.

19. A body care preparation comprising a wax dispersion according to claim 12.

20. A process for the production of a wax dispersion having a particle size distribution such that 50% of the dispersed wax is <10 micrometers (μm), and having (a) 10-75% by weight, based on the wax dispersion, of a wax phase with a melting point in the range of about 35 to about 50° C., which comprises at least one oil or wax component selected from the group consisting of dialkyl(ene) carbonates, dicarboxylic acids, hydroxyfatty alcohols, and mixtures thereof and at least one emulsifier; and (b) a water phase, said process comprising:
   (1) providing a preliminary emulsion of the wax phase containing a water phase and having a temperature above the melting range of the waxes, and (2) introducing said preliminary emulsion, under pressure, into a polymer-containing water phase which has a temperature in the range of about 1 to 30° C.

21. The process according to claim 20, further comprising homogenizing the preliminary emulsion at least once before introducing it into the water phase of step (2).

22. The process according to claim 20, further comprising cooling the preliminary emulsion in a heat exchanger before introducing it into the water phase of step (2).

23. The process according to claim 20, wherein the preliminary emulsion also contains a polymer.

24. The process according to claim 23, wherein the polymer is selected from the group consisting of polyacrylates, polysaccharides, polyacrylamides, and mixtures thereof.

25. The process according to claim 20, wherein the preliminary emulsion is introduced into the water phase of step (B) by spraying under pressure through a nozzle.

* * * * *